(12) United States Patent
Adkins et al.

(10) Patent No.: US 7,408,473 B2
(45) Date of Patent: Aug. 5, 2008

(54) METHOD OF COHB CALCULATION IN A CARBON MONOXIDE DETECTOR

(75) Inventors: Charles D. Adkins, Plain City, OH (US); John G. Chapman, Delaware, OH (US); Timothy D. Kaiser, Plain City, OH (US)

(73) Assignee: Maple Chase Company, Farmington, CT (US)

( * ) Notice: Subject to any disclaimer, the term of this patent is extended or adjusted under 35 U.S.C. 154(b) by 82 days.

(21) Appl. No.: 11/361,941

(22) Filed: Feb. 24, 2006

(65) Prior Publication Data

US 2007/0200719 A1 Aug. 30, 2007

(51) Int. Cl.
*G08B 17/10* (2006.01)

(52) U.S. Cl. .................. 340/632; 340/603; 73/23.2; 73/31.01

(58) Field of Classification Search .............. 340/632, 340/627, 603; 73/23.2, 31.01, 31.02, 31.03
See application file for complete search history.

(56) References Cited

U.S. PATENT DOCUMENTS

| | | | | |
|---|---|---|---|---|
| 4,860,223 A | * | 8/1989 | Grilk | 702/19 |
| 4,896,143 A | | 1/1990 | Dolnick et al. | |
| 5,526,280 A | * | 6/1996 | Consadori et al. | 702/24 |
| 5,786,768 A | * | 7/1998 | Chan et al. | 340/632 |
| 5,969,623 A | * | 10/1999 | Fleury et al. | 340/632 |
| 6,433,696 B1 | * | 8/2002 | Deiterman et al. | 340/632 |
| 6,436,712 B1 | * | 8/2002 | Yurgil et al. | 436/55 |
| 6,819,252 B2 | | 11/2004 | Johnston et al. | |
| 7,242,309 B2 | * | 7/2007 | Yokosawa et al. | 340/632 |

OTHER PUBLICATIONS

"Carbon Monoxide Alarms", Underwriter's Laboratory UL 2034 Carbon Monoxide Exposure Specification, pp. 17-37, Oct. 15, 1997.

* cited by examiner

*Primary Examiner*—Jeff Hofsass
*Assistant Examiner*—Kerri L McNally
(74) *Attorney, Agent, or Firm*—Andrus, Sceales, Starke & Sawall, LLP

(57) ABSTRACT

A gas detector and method of operating the gas detector that includes a carbon monoxide sensor and a processor. The carbon monoxide sensor senses an environmental concentration of carbon monoxide and provides the sensed value to the processor. Upon receiving the value of the carbon monoxide level (COppm), the processor determines an alarm threshold level based upon the COppm level. Once the alarm threshold level is determined, the processor calculates the COHb percentage for the current COppm reading based upon a derived, fixed point equation. The processor activates an audible/visual indicator when the sensed COHb percentage exceeds the alarm threshold.

20 Claims, 5 Drawing Sheets

| Coppm | Time to Alarm | CO % Alarm Threshold |
|---|---|---|
| 45 | No Alarm* | |
| 48 | 606.75 | |
| 50 | 304.15 | |
| 53 | 222.75 | 8% |
| 55 | 195.25 | |
| 57 | 174.5 | |
| 59 | 158.75 | |
| 61 | 145.75 | |
| 63 | 135 | |
| 65 | 168.75 | |
| 75 | 120.5 | |
| 85 | 95.75 | 9% |
| 95 | 79.5 | |
| 99 | 74.14 | |
| 105 | 67.75 | |
| 106 | 42.25 | |
| 115 | 38 | |
| 135 | 30.75 | |
| 145 | 28.25 | |
| 150 | 27.5 | |
| 160 | 25 | |
| 200 | 20 | |
| 300 | 13 | 6.5% |
| 400 | 9.25 | |
| 420 | 8.5 | |
| 500 | 7.25 | |
| 600 | 6.25 | |
| 700 | 5.25 | |
| 800 | 4.25 | |
| 1023 | 3.75 | |

*FIG. 4*

| CO ppm | UL REQUIREMENT | | | DETECTOR | | |
|---|---|---|---|---|---|---|
| | MINIMUM | MAXIMUM | MEDIAN | FAST | ACTUAL | SLOW |
| 30 | <30 days | NEVER | | | NEVER | |
| 54 | | | | | 672.5 | |
| 60 | | | | 197 | 219 | 241 |
| 70 | 60 | 240 | 150 | | 139.5 | |
| 80 | | | | 95.4 | 106 | 116 |
| 140 | | | | 27 | 29.75 | 32.75 |
| 150 | 10 | 50 | 30 | | 27.5 | |
| 160 | | | | 22.72 | 25 | 27.5 |
| 380 | | | | 8.86 | 9.75 | 10.72 |
| 400 | 4 | 15 | 9.5 | | 9.25 | |
| 420 | | | | 7.72 | 8.5 | 9.35 |
|  | 58 | 56 | 62 | | 60 | |

FIG. 5

| Precent COHB | | Hex | | Decimal |
|---|---|---|---|---|
| 6.5 | | 680000 | | 6815744 |
| 8 | | 800000 | | 8388608 |
| 8.5 | | 880000 | | 8912893 |
| 8.75 | | 8C0000 | | 9175040 |
| 9 | | 900000 | | 9437184 |

Scale Factor = 2^20 = 1048576 (decimal) = 100000 (hex)

FIG. 6

METHOD OF COHB CALCULATION IN A CARBON MONOXIDE DETECTOR

BACKGROUND OF THE INVENTION

The present invention relates to the operation of a carbon monoxide detector. More specifically, the present invention relates to a method of operating a processor within a carbon monoxide sensor to reduce the calculation complexity required for estimating the COHb percentage.

Currently, natural gas and liquefied petroleum gases are used widely as fuel for domestic, commercial and industrial heating and cooking applications. The wide use of these gases for heating and cooking purposes creates a danger of leakage, which will contaminate the surrounding environment, creating dangerous conditions. In many applications, carbon monoxide is created as a byproduct of the combustion process. Carbon monoxide is an odorless and colorless gas, thus rendering contaminating levels difficult to detect by an individual. Carbon monoxide is absorbed into an individual's lungs and reacts with the hemoglobin in the blood to form carboxyhemoglobin (COHb), which reduces the oxygen carrying capacity of the blood. Thus, the presence of carbon monoxide in an environment above certain levels is extremely dangerous and can easily poison individuals unaware of its presence.

The uptake of carbon monoxide by a human is a function of both the time of exposure to the carbon monoxide as well as the concentration of the carbon monoxide within the atmosphere. The equation for determining the percentage of COHb in a person's blood can be represented by the Coburn, Forster & Kane Equation, which is set forth below.

$$\% COHB_t = \% COH_o(e^{-(t/2398B)}) + 218(1-e^{-(t/2398B)}) \\ (0.0003 + CO_{ppm}/1316) \quad (1)$$

In the above equation, the variable B is set 0.0404 for representing an individual in a heavy work environment, in which the individual is consuming a relatively large volume of oxygen, while the variable t represents the time in minutes.

A person is in danger of carbon monoxide poisoning when the percentage of COHb in the blood increases due to the continued exposure to carbon monoxide, such as the 10% level set by the Underwriter's Laboratory UL 2034 Carbon Monoxide Exposure Specification. According to the UL 2034 specification, at concentration levels of 70 ppm, a carbon monoxide detector must respond with an alarm within 60-240 minutes. At elevated concentration levels of 400 ppm, the detector must respond with an alarm within an interval of 4-15 minutes.

Although the Coburn, Forster & Kane Equation set forth above is accurate for determining the percent of COHb in a person's blood, the calculation required is very complex and requires a sophisticated and powerful processor for carrying out the complex math operations required to find the solution for the equation. Such complicated math would require extensive math libraries, thus drastically increasing the code size required within the processor operating the carbon monoxide detector. Since many carbon monoxide detectors are battery powered, the increases processor capabilities and additional program memory required to carry out the COHb calculation will result in both higher cost for the product and decreased battery life.

Therefore, a need exists for a method of operating a carbon monoxide detector that reduces the complexity of the COHb calculation while still operating to generate an alarm in accordance with UL standards.

SUMMARY OF THE INVENTION

The present invention is an adverse condition detector and method of operating the detector to calculate the carboxyhemoglobin (COHb) level utilizing a fixed point equation that accurately approximates the more complicated and complex Coburn, Forster & Kane Equation such that the detector operates within the parameters set forth by the UL 2034 standard. The detector utilizes a fixed point algorithm that calculates COHb levels based upon the current carbon monoxide concentration level (COppm) detected.

The adverse condition detector includes a carbon monoxide sensing circuit that is operable to detect the concentration of carbon monoxide in an area surrounding the detector. The carbon monoxide circuit sends an electrical signal to a processor of the adverse condition detector that is related to the concentration of carbon monoxide in the area surrounding the detector.

Upon receiving the electrical signal, the processor converts the signal to a concentration level of carbon monoxide. Based upon the carbon monoxide concentration level, the processor calculates a COHb level utilizing a fixed point equation that approximates the Coburn, Forster & Kane calculation without utilizing complex mathematical formulas. The equation utilized by the processor calculates the COHb level based upon the current CO concentration level and the past calculated value of the COHb level. The equation utilizes a scale factor and variables based off of the scale factor, resulting in a fixed point equation that does not require complex mathematical equations or mathematical tables.

Once the current COHb level has been calculated, the processor compares the calculated level of COHb to a COHb alarm threshold level. In accordance with the invention, multiple COHb alarm threshold levels are stored in a memory location, where each of the COHb alarm threshold levels are assigned to a range of carbon monoxide concentration levels. Based upon the current carbon monoxide concentration level, the processor selects one of the COHb alarm threshold levels and compares the calculated COHb level to the selected COHb alarm threshold level.

If the calculated COHb level exceeds the selected COHb alarm threshold level, the processor actuates an alarm device, such as an audible horn. The audible horn remains active until the calculated COHb level falls below the COHb alarm threshold for the current level of carbon monoxide concentration.

In one embodiment of the invention, the detector includes three different COHb alarm threshold levels for different concentrations of carbon monoxide. The different levels of alarm thresholds allows a processor utilizing the method of the invention to approximate the Coburn, Forster & Kane Equation and meet the specification set forth by UL 2034.

BRIEF DESCRIPTION OF THE DRAWINGS

The drawings illustrate the best mode presently contemplated of carrying out the invention. In the drawings:

FIG. 4 is a table illustrating the Time to Alarm for multiple alarm thresholds utilizing the method of the present invention;

FIG. 5 is a table illustrating the Time to Alarm requirements under UL 2034 versus the Time to Alarm specifications for a CO detector operating under the present invention; and FIG. 6 is a table illustrating the hexadecimal representation of the various COHb alarm limits.

DETAILED DESCRIPTION OF THE INVENTION

Figure 1:
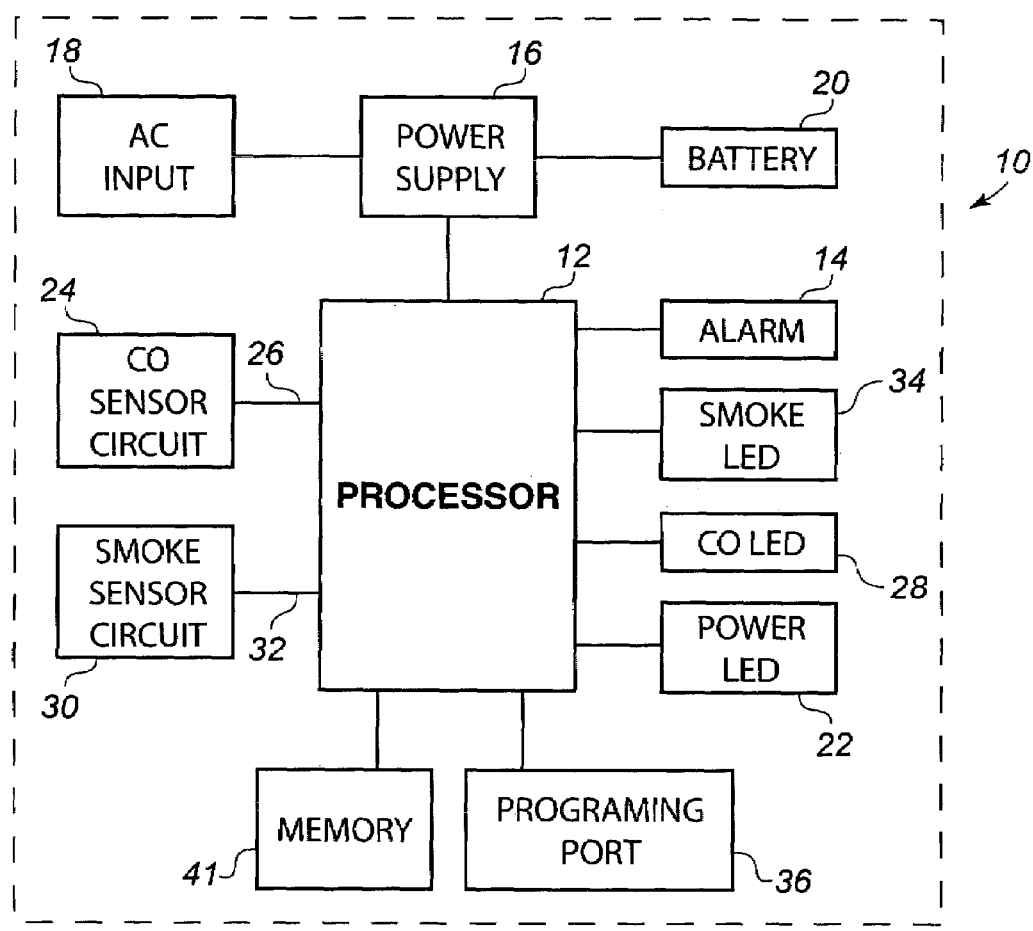
FIG. 1 is a schematic block diagram of a carbon monoxide alarm in accordance with the present invention.

FIG. 1 illustrates an adverse condition detector 10 that operates in accordance with the present invention. In the embodiment of the invention illustrated in FIG. 1, the adverse condition detector is a combination smoke and CO detector. However, the adverse condition detector 10 could be a stand alone carbon monoxide (CO) detector while operating within the scope of the present invention.

The adverse condition detector 10 includes a central processor 12 that controls the operation of the adverse condition detector 10. In the preferred embodiment of the invention, the processor 12 is available from Atmel Mega 32, although other processors could be utilized while operating within the scope of the present invention. The block diagram of FIG. 1 is shown on an overall schematic scale only, since the actual circuit components for the individual blocks of the diagram are well known to those skilled in the art and form no part of the present invention.

As illustrated in FIG. 1, the adverse condition detector 10 includes an alarm indicator or transducer 14 for alerting a user that an adverse condition has been detected. Such an alarm indicator or transducer 14 could include but is not limited to a horn, buzzer, siren, flashing lights or any other type of audible or visual indicator that would alert a user of the presence of the adverse condition. In the embodiment of the invention illustrated, the alarm indicator 14 is a piezoelectric resonant horn, which is a highly efficient device capable of producing an extremely loud (85 db) alarm when driven by a relatively small drive signal.

The processor 12 is driven by a power supply circuit 16 that is coupled to both an AC power source 18 and a battery back-up 20. The power supply provides electrical power to the processor 12 from the AC input 18 during normal conditions and utilizes the battery 20 as a back-up when the AC input 18 has been interrupted. The detector includes a power LED 22 that allows the user to quickly determine that proper AC power is being supplied to the detector 10.

In the embodiment of the invention illustrated in FIG. 1, the adverse condition detector 10 is a combination smoke and carbon monoxide detector. The detector includes a carbon monoxide sensor circuit 24 coupled to the processor 12 by an input line 26. Preferably, the carbon monoxide sensor circuit 24 includes a carbon monoxide sensor, such as is conventionally available from Monox under model name Mark IV. The electrical characteristics of the carbon monoxide sensor change based upon the CO concentration levels in the environment in which the sensor is located. The CO sensor circuit 24 supplies the changing electrical signal to the processor 12, which can then determine the concentration of the carbon monoxide in the environment in which the detector 10 is located. Based upon the carbon monoxide concentration level detected, the processor 12 will selectively generate a signal to the alarm 14 as well as to the carbon monoxide LED 28. The operation of the processor 12 to calculate when the alarm 14 and the CO LED 28 are activated will be described in much greater detail below.

In addition to the carbon monoxide sensor circuit 24, the adverse condition detector 10 also includes a smoke sensor circuit 30 coupled to the processor 12. The smoke sensor circuit 30 can be either a photoelectric or ionization smoke sensor that detects the presence of smoke within the area in which the adverse condition detector 10 is located.

When the smoke sensor circuit 30 senses a level of smoke that exceeds a selected value, the smoke sensor circuit 30 generates a smoke signal along line 32 that is received by the processor 12. Upon receiving the smoke signal, the processor 12 generates an alarm signal to the alarm indicator 14 as well as activates the smoke LED 34.

Figure 2:
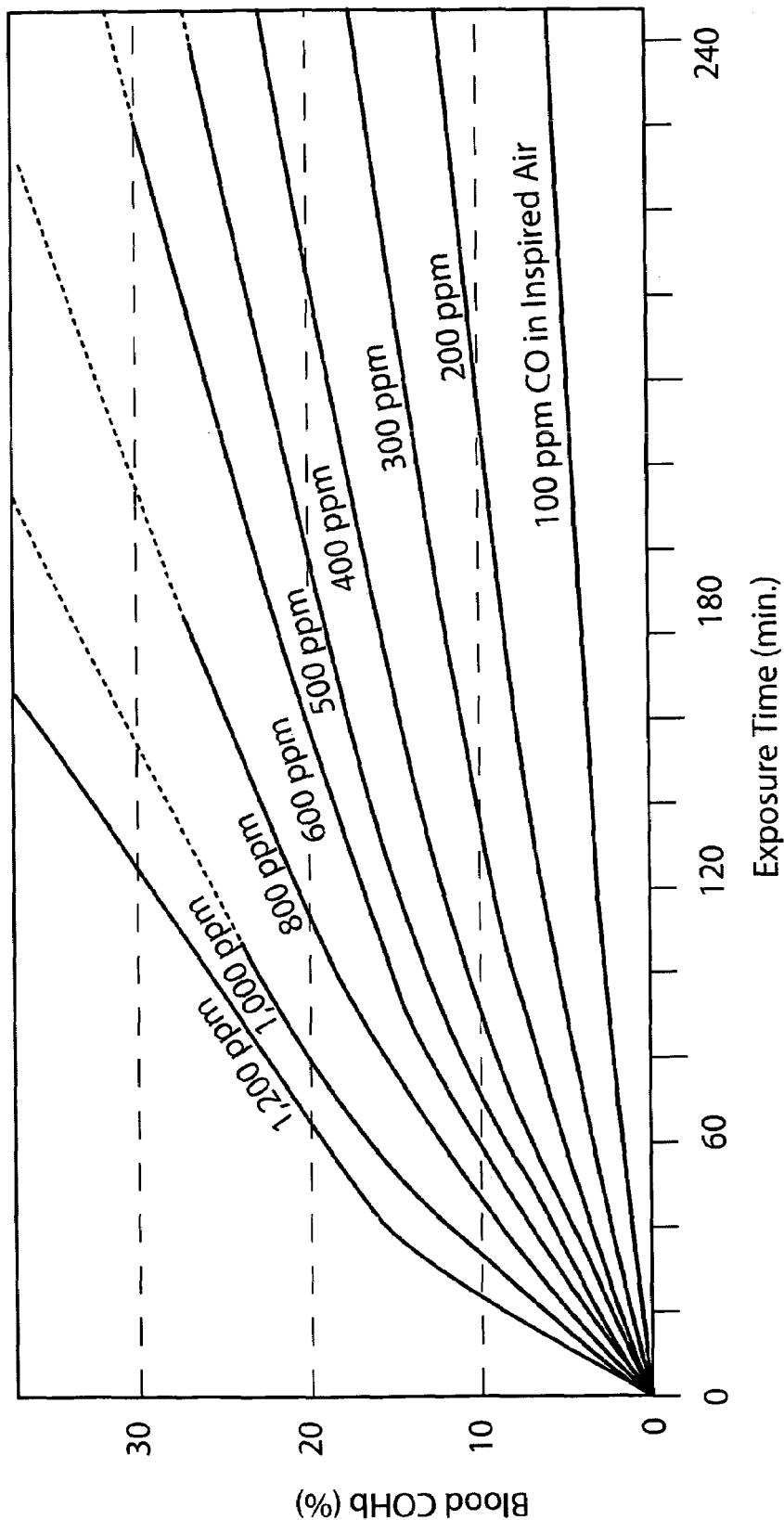
FIG. 2 is a graph of COHb equilibrium levels versus exposure time for multiple CO concentration levels.

As described previously, the processor 12 determines whether a hazardous environmental CO concentration exists by computing a carboxyhemoglobin (COHb) level that would exist in a person's blood that is exposed to the CO concentration level. The COHb level that would exist is a function of both the environmental CO concentration and the exposure time to that CO concentration, as well as the COHb level, if any, that existed in the person previously. The COHb level in the bloodstream is represented by the percentage of COHb relative to all hemoglobin in the bloodstream and increases as a function of the environmental CO concentration and exposure time. FIG. 2 illustrates the blood COHb percentage as a function of exposure time for various CO concentration levels referred to in parts per million (ppm). Hereinafter, the environmental CO concentration in parts per million will be referred to as COppm.

COHb danger levels are set by Underwriters Laboratory specification UL 2034. Under this UL specification, a carbon monoxide detector must activate when the COHb level reaches 10%. During testing of adverse condition detectors, UL subjects the detector to carbon monoxide concentration levels at three different concentrations (70, 150 and 400 ppm). At each of these levels, the detector must respond within maximum and minimum time periods, which are set forth in columns 56 and 58 of FIG. 5.

The most widely recognized equation for determining the percentage of COHb in a person's blood at a given time is represented by the Coburn, Forster & Kane Equation set forth below and referred to as Equation (1):

$$\% \ COHB_t = \% \ COH_o(e^{-(t/2398B)}) + 218(1 - e^{-(t/2398B)})(0.0003 + CO_{ppm}^o/1316) \quad (1)$$

In Equation (1), the current COHb percentage at time t is related to the percentage of COHb at time 0 and depends upon the current CO level as well as the time of exposure to the carbon monoxide. For the UL 2034 standard, the variable B is set at 0.0404, which represents a person in a heavy work effort.

Although the above formula functions well to determine the current percent of COHb in a person, the calculation requires complex mathematical formulas that, if implemented exactly as specified, require extensive math libraries that would drastically increase code size within the processor. The increase in the code size translates to a more powerful processor and additional program memory, resulting in higher costs for the detector. Further, the powerful processor would also result in higher power requirements, thus decreasing the effective battery life for the detector.

In accordance with the present invention, the processor 12 of the adverse condition detector 10 is configured to perform a fixed point mathematical calculation to estimate the COHb level relative to the current COppm level detected by the CO sensor circuit. The fixed point mathematical formula simplifies the Coburn, Forster & Kane Equation and is represented below as Equation (2):

$$Z*COHb = A*COHb(\text{prev}) + B + C*CO_{ppm}\text{Reading} \quad (2)$$

Where the constants are shown below:

Scale Factor $Z=2^{20}=1048576$ $A=1043178=1048576*0.9948522=e^{(-t/(2398*0.0404))}$ where $t=0.5$ min.

$B=353=1048576*(1-0.994852)*218*0.0003$ $C=894=1048576*(1-0.994852)*218/1316$

In the equation above, the scale factor Z is selected as $2^{20}$, which corresponds to the decimal value 1048576 and the hexadecimal value 100000. The scale factor gives a resolution of approximately 0.000001. Although a specific scale factor was selected for the preferred embodiment of the invention, any appropriate scale factor can be utilized while operating within the scope of the present invention.

As can be seen by the above equation, the sampling by the CO sensor circuit and the processor is carried out at approximately 30 second intervals such that the variable t is represented by 0.5. If the time base is changed, the equations will be recalculated. However, the approach of the present invention is flexible such that different time variables can be utilized.

As can be understood by Equation (2), the values for the scale figure and the coefficients A, B and C are integers that can be represented in hexadecimal format. The representation of the various variables and COHb levels using hexadecimal representation allows the processor to operate without requiring complex mathematical formulas and stored variable tables.

As shown in FIG. 6, the COHb level is represented for five different levels, each of which is less than the 10% value required by the UL 2034 standard. Each of these levels is represented by both a hexadecimal and a decimal equivalent.

During the operation of the processor, a COHb alarm level is programmed into the microprocessor for various COppm levels returned to the processor by the CO sensor circuit. Depending upon the COppm level, an alarm threshold level is selected within the processor, and the processor 12 will generate an alarm signal when the COHb level determined by Equation 2 exceeds the COHb alarm threshold.

In the preferred embodiment of the invention, different COHb alarm threshold levels are set based upon the sensed COppm level. In the most preferred embodiment, the alarm threshold level is set at 8% when the COppm is less than or equal to 63 ppm. The alarm threshold level is set at 9% when the COppm is between 63 and 105. The third and final alarm threshold level is set at 6.5% when the COppm is greater than or equal to 106. These values are shown in FIG. 4.

As further shown in FIG. 4, the Time to Alarm at the various COppm levels detected by the adverse condition detector 10 are shown for the different alarm threshold levels. The three alarm threshold levels (8, 9 and 6.5%) are shown as the most preferred embodiment of the invention. However, it is contemplated that various alarm thresholds could be used while operating within the scope of the present invention. As an example, the alarm threshold could be selected at 8.5% for COppm levels less than or equal to 115 and 6.5% for COppm levels greater than 115. These two alarm levels would also result in operation of the detector within the parameter set by the UL 2034 standard.

When the adverse condition detector is initially manufactured, the alarm levels are programmed into the processor. These alarm levels are preselected and control the activation of the alarm based upon the electrical signal received from the carbon monoxide sensor circuit. Alternatively, it is contemplated that the processor 12 could include a programming port 36 (FIG. 1) that would allow the alarm parameters to be adjusted after the detector has been manufactured and placed into service.

Figure 3:
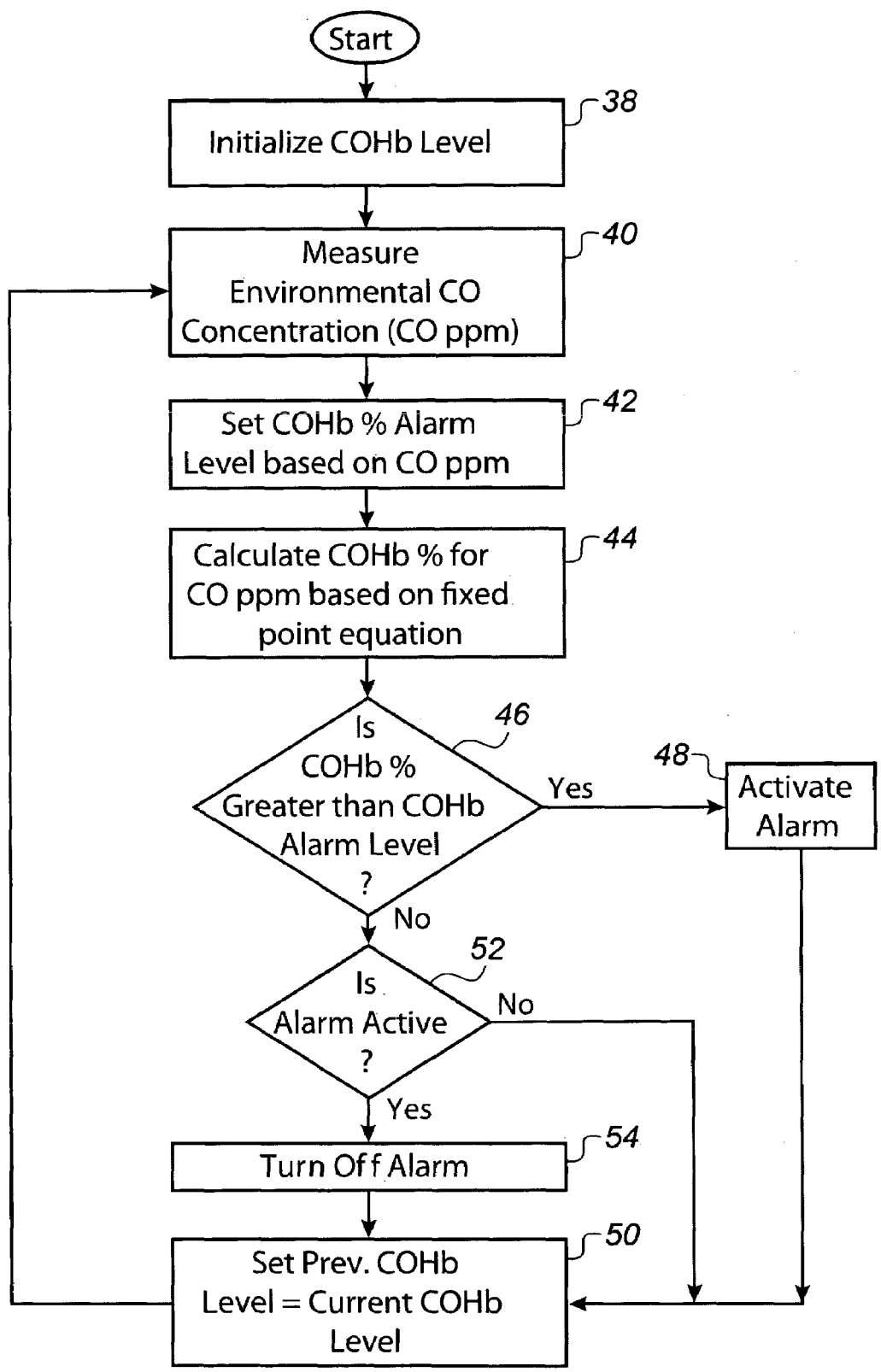
FIG. 3 is a flow diagram illustrating the steps performed by the processor of the CO detector.

FIG. 3 is a flowchart illustrating the software routine steps running on the processor 12 to determine the COHb levels from the measured environmental CO concentration (COppm). When the detector 10 is initially turned on, the "previous" level for the COHb is set to a predetermined minimum level, such as 0% as shown in step 38. After the previous level for the COHb has been set, the detector obtains the environmental CO concentration COppm from the CO sensor circuit 24, as shown in step 40. In the preferred embodiment of the invention, the environmental CO concentration COppm is obtained in thirty second intervals and is received at the processor as an electrical signal.

After the environmental CO concentration COppm has been received, the processor retrieves the COHb alarm threshold level from memory 41 based upon the current COppm level sensed in the step 40. As illustrated in FIG. 4, the alarm threshold level in the preferred embodiment of the invention varies depending upon the level of the COppm measurement. Specifically, the alarm threshold level has three different values depending upon the current sensed value for the COppm.

Once the alarm threshold level has been determined in step 42, the processor utilizes Equation (2) to calculate the current COHb percentage for the COppm level sensed, as illustrated in step 44. As illustrated in FIG. 6, the COHb alarm threshold for various COHb percentages are represented in hexadecimal form such that the entire calculation using Equation (2) can be carried out using fixed point mathematics.

In step 46, the processor determines whether the COHb percentage determined by Equation (2) is greater than the COHb alarm threshold level for the current COppm being sensed by the CO sensor circuit 24. If the COHb level calculated by Equation (2) is greater than the alarm threshold level, the processor activates the alarm in step 48 and the COHb (prev) is set to be the COHb level calculated during the last iteration utilizing Equation (2), as illustrated by step 50. After the value for the COHb (prev) is set, the processor returns to step 40 to once again measure the environmental CO concentration level COppm. The process is then repeated until the processor determines in step 46 that the calculated COHb percentage is no longer greater than the COHb alarm threshold level in step 46.

Based upon the configuration of Equation (2), the calculated value for the COHb percentage will decrease in an exponential manner such that the time to clear the alarm for various COppm levels will be different. As an example, if the COppm level is 95, the time to clear the alarm will be approximately 10.25 minutes. However, if the COppm level is 1023 when the alarm was generated, the time to clear the alarm will be 42.75 minutes.

After step 46, if the processor determines that the calculated COHb percentage is less than the alarm threshold level, the processor then determines in step 52 whether the detector alarm is currently active. If the alarm is not active, the COHb (prev) is set to be the current COHb level in step 50 and the processor again returns to step 40 to measure the COppm level at the next 0.5 minute interval.

If the processor determines at step 52 that the alarm is currently active, the processor will turn off the alarm in step 54, since the calculated COHb percentage has fallen below the COHb threshold alarm level for the measured COppm level. Following step 54, the processor again sets the COHb (prev) level to equal the current COHb level determined by Equation 2.

FIG. 5 illustrates the maximum, minimum and median Time to Alarm guideline set forth by UL 2034 standards. The Time to Alarm values are shown for the three UL testing levels of 70, 150 and 400 ppm. The maximum and minimum columns 56, 58 illustrate the two extremes acceptable under the UL requirement for a carbon monoxide detector. Column 60 of the table in FIG. 5 illustrates the Time to Alarm values for a carbon monoxide detector operating utilizing the calculations from Equation (2) with the three alarm threshold levels shown in FIG. 4. As Column 60 indicates, the detector will alarm at values close to the median 62 and thus will satisfy the UL 2034 standard.

As can be understood by the above description, a small processor of 8 bits, for example, can accomplish the calculations used to determine the alarm thresholds and activate the carbon monoxide detector to satisfy the UL 2034 requirements.

We claim:

1. A method of operating an adverse condition detector, the method comprising the steps of:
   measuring the current concentration level of carbon monoxide in an area surrounding the detector;
   calculating a carboxyhemoglobin (COHb) percentage level utilizing a fixed point equation based upon the current carbon monoxide concentration level;
   setting a COHb alarm threshold level based upon the current concentration level of carbon monoxide; and
   generating an alarm when the calculated COHb level exceeds the COHb alarm threshold level.

2. The method of claim 1 further comprising the steps of:
   setting a plurality of COHb alarm threshold levels, each COHb alarm threshold level being associated with a range of carbon monoxide concentration levels; and
   selecting one of the plurality of COHb alarm threshold levels based upon the current carbon monoxide concentration level.

3. The method of claim 1 wherein the COHb percentage level is calculated by the fixed point equation:

$$Z*COHb = A*COHb(\text{prev}) + B + C*COppm\text{Reading}$$

where Z, A, B and C are constants.

4. The method of claim 3 wherein Z, A. B and C are selected as:
   $Z = 2^{20} = 1048576$
   $A = 1043178 = 1048576*0.9948522 = e^{(-t/(2398*0.0404))}$ where $t = 0.5$ min.
   $B = 353 = 1048576*(1-0.994852)*218*0.0003$
   $C = 894 = 1048576*(1-0.994852)*218/1316$.

5. The method of claim 2 wherein the plurality of COHb alarm threshold levels are stored in a memory device.

6. A method of operating an adverse condition detector, the method comprising the steps of:
   measuring the current concentration level of carbon monoxide in an area surrounding the detector;
   calculating a carboxyhemoglobin (COHb) percentage level based upon the current carbon monoxide concentration level;
   setting a plurality of COHb alarm threshold levels, wherein a first COHb alarm threshold is set at a first level for carbon monoxide concentration levels below a first concentration value, a second COHb alarm threshold is set at a second level for carbon monoxide concentration levels between the first concentration value and a second concentration value, and a third COHb alarm threshold level is set at a third level for carbon monoxide concentration levels above the second concentration value;
   selecting one of the plurality of COHb alarm threshold levels based upon the current carbon monoxide concentration level; and
   generating an alarm when the calculated COHb level exceeds the selected COHb alarm threshold level.

7. The method of claim 6 wherein the first COHb alarm threshold level is about 8% for carbon monoxide concentration levels below about 63 ppm, the second COHb alarm threshold level is about 9% for carbon monoxide concentration levels between 64 and 105 ppm, and the third COHb alarm threshold level is about 6.5% for carbon monoxide concentration levels above 105 ppm.

8. The method of claim 1 wherein the COHb percentage level is calculated at regular time intervals.

9. The method of claim 8 wherein the calculated COHb percentage level is based on the COHb concentration level calculated during the previous time interval.

10. A carbon monoxide detector, comprising:
    a carbon monoxide sensor for measuring the CO concentration in an area surrounding the detector; and
    a processor coupled to the carbon monoxide sensor for receiving the measured CO concentration, the processor being operable to calculate the carboxyhemoglobin (COHb) level corresponding to the measured CO concentration utilizing a fixed point equation and to compare the calculated COHb level to a COHb alarm threshold level,
    wherein the COHb alarm threshold level is selected from a plurality of stored COHb alarm threshold levels based upon the value of the measured CO concentration.

11. The detector of claim 10 wherein each of the COHb alarm threshold levels are associated with a range of CO concentration levels.

12. A carbon monoxide detector, comprising:
    a carbon monoxide sensor for measuring the CO concentration in an area surrounding the detector; and
    a processor coupled to the carbon monoxide sensor for receiving the measured CO concentration, the processor being operable to calculate the carboxyhemoglobin (COHb) level corresponding to the measured CO concentration and to compare the calculated COHb level to a COHb alarm threshold level,
    wherein the COHb alarm threshold level is selected from a plurality of stored COHb alarm threshold levels based upon the value of the measured CO concentration, wherein a first COHb alarm threshold is set at a first level for carbon monoxide concentration levels below a first concentration value, a second COHb alarm threshold is set at a second level for carbon monoxide concentration levels between the first concentration value and a second concentration value, and a third COHb alarm threshold level is set at a third level for carbon monoxide concentration levels above the second concentration value.

13. The detector of claim 12 wherein a first COHb alarm threshold level is about 8% for carbon monoxide concentration levels below about 63 ppm, a second COHb alarm threshold level is about 9% for carbon monoxide concentration levels between 64 and 105 ppm, and a third COHb alarm threshold level is about 6.5% for carbon monoxide concentration levels above 105 ppm.

14. The detector of claim 10 wherein the COHb percentage levels are calculated at regular time intervals.

15. The detector of claim 14 wherein the calculated COHb percentage level is based on the COHb concentration calculated during the previous time interval.

16. The detector of claim 11 wherein the plurality of COHb alarm threshold levels are stored in a memory accessible by the processor.

17. The detector of claim 10 further comprising an alarm device coupled to the processor, wherein the alarm device is actuated when the calculated COHb level exceeds the selected COHb alarm threshold.

18. The detector of claim 10 wherein the COHb percentage level is calculated by the fixed point equation:

$$Z*COHb=A*COHb(prev)+B+C*COppm\text{Reading}$$

where Z, A, B and C are constants.

19. The detector of claim 18 wherein Z, A, B and C are selected as:

Z=2^20=1048576
A=1043178=1048576*0.9948522=e^(−t/(2398*0.0404)) where t=0.5 min.
B=353=1048576*(1−0.994852)*218*0.0003
C=894=1048576*(1−0.994852)*218/1316.

20. The detector of claim 10 wherein the carbon monoxide sensor generates an electrical signal related to the level of carbon monoxide measured in the area surrounding the detector.

* * * * *